(12) United States Patent
McCrory et al.

(10) Patent No.: US 6,589,199 B1
(45) Date of Patent: Jul. 8, 2003

(54) SYSTEM FOR IMPLANTING A CROSS-LINKED POLYSACCHARIDE FIBER AND METHODS OF FORMING AND INSERTING THE FIBER

(75) Inventors: Jennifer McCrory, Sunnyvale, CA (US); Patrik Lüscher, Pfäffikon (CH); Kalpana Kamath, Natick, MA (US); Ronald Sahatjian, Lexington, MA (US)

(73) Assignee: Boston Scientific Corporation, Natick, MA (US)

(*) Notice: Subject to any disclaimer, the term of this patent is extended or adjusted under 35 U.S.C. 154(b) by 0 days.

(21) Appl. No.: 09/538,152

(22) Filed: Mar. 29, 2000

Related U.S. Application Data

(60) Division of application No. 08/919,107, filed on Aug. 28, 1997, now Pat. No. 6,139,520, which is a continuation-in-part of application No. 08/776,943, filed as application No. PCT/CH95/00184 on Aug. 16, 1995, now Pat. No. 6,296,632.

(30) Foreign Application Priority Data

Aug. 17, 1999 (CH) .............................................. 2533/94

(51) Int. Cl.⁷ ................................................ A61F 13/20
(52) U.S. Cl. ............................ 604/13; 604/11; 604/502
(58) Field of Search ......................... 606/1, 108, 151, 606/191–200, 213; 604/11–19, 502, 48, 500; 128/898

(56) References Cited

U.S. PATENT DOCUMENTS

| | | | |
|---|---|---|---|
| 2,524,195 A | 10/1950 | Hoover | |
| 3,431,907 A | 3/1969 | Lubet-Moncla | |
| 3,703,174 A | 11/1972 | Smith | |
| 3,826,256 A | 7/1974 | Smith | |
| 3,906,550 A | 9/1975 | Rostoker et al. | |
| 4,159,022 A | 6/1979 | Pevsner | |
| 4,237,885 A | 12/1980 | Wong et al. | |
| 4,402,308 A | 9/1983 | Scott | |
| 4,512,338 A | 4/1985 | Balko et al. | |
| 4,551,132 A | 11/1985 | Pasztor et al. | |

(List continued on next page.)

FOREIGN PATENT DOCUMENTS

| | | |
|---|---|---|
| DE | 31 15763 | 11/1982 |
| EP | 0186632 | 7/1986 |
| EP | 0 424 068 A2 | 4/1991 |
| EP | 0621020 | 10/1994 |
| FR | 2696636 | 4/1994 |

(List continued on next page.)

OTHER PUBLICATIONS

Taki, K., "Possibility and Limit of Intravascular Surgery"; Medical Tribune, pp. 46–47, Oct. 1989, Nippon Accel Shubringer Shuppan, K.K.
Bernatchez et al., "Biocompatibility of a New Semisolid Bioerodible Poly (ortho ester) Intended for the Ocular Delivery of 5–fluorouracil"; Journal of Biomedical Materials Research; vol. 28; No. 9, pp. 1037–1046, Sep., 1994.

(List continued on next page.)

*Primary Examiner*—Glenn K. Dawson
(74) *Attorney, Agent, or Firm*—Finnegan, Henderson, Farabow, Garrett & Dunner LLP

(57) ABSTRACT

Systems and methods are disclosed for implanting and forming both a polysaccharide fiber and an implant formed of the fiber. In one system, a liquid including polysaccharide and a liquid including a cross linking agent are mixed in a cannula to form a cross linked polysaccharide fiber in the cannula. In another system, a carrier fluid delivers a previously manufactured fiber through a cannula. A cutter is optionally provided on the cannula to sever the fiber after a sufficient length of fiber is implanted.

9 Claims, 5 Drawing Sheets

U.S. PATENT DOCUMENTS

| | | | |
|---|---|---|---|
| 4,712,553 A | 12/1987 | MacGregor | |
| 4,820,267 A | 4/1989 | Harman | |
| 4,820,767 A | 4/1989 | Wu | |
| 4,840,622 A | 6/1989 | Hardy | |
| 4,932,942 A | 6/1990 | Maslanka | |
| 4,950,295 A | 8/1990 | Weigum et al. | |
| 4,979,942 A | 12/1990 | Wolf et al. | |
| 4,994,069 A | 2/1991 | Ritchart et al. | |
| 5,021,059 A | 6/1991 | Kensey et al. | |
| 5,074,840 A | 12/1991 | Yoon | |
| 5,100,392 A | 3/1992 | Orth et al. | |
| 5,211,627 A | 5/1993 | William | |
| 5,250,071 A | 10/1993 | Palermo | |
| 5,256,146 A | 10/1993 | Ensminger et al. | |
| 5,263,927 A | 11/1993 | Shlain | |
| 5,308,342 A | 5/1994 | Sepetka et al. | |
| 5,318,524 A | 6/1994 | Morse et al. | |
| 5,322,510 A | 6/1994 | Lindner et al. | |
| 5,336,263 A | 8/1994 | Ersek et al. | |
| 5,374,261 A | 12/1994 | Yoon | |
| 5,376,118 A | 12/1994 | Kaplan et al. | |
| RE34,866 E | 2/1995 | Kensey et al. | |
| 5,443,454 A | 8/1995 | Tanabe et al. | |
| 5,454,833 A | 10/1995 | Boussignac et al. | |
| 5,514,158 A | 5/1996 | Kanesaka | |
| 5,522,795 A | 6/1996 | Green et al. | |
| 5,522,822 A | 6/1996 | Phelps et al. | |
| 5,531,735 A * | 7/1996 | Thompson | 604/891.1 |
| 5,545,169 A | 8/1996 | Yarger | |
| 5,571,189 A | 11/1996 | Kuslich | |
| 5,575,815 A | 11/1996 | Slepian et al. | |
| 5,591,224 A | 1/1997 | Schwartz et al. | |
| 5,614,204 A | 3/1997 | Cochrum | |
| 5,660,854 A | 8/1997 | Haynes et al. | |
| 5,667,778 A | 9/1997 | Atala | |
| 5,690,666 A | 11/1997 | Berenstein et al. | |
| 5,746,747 A | 5/1998 | McKeating | |
| 5,766,160 A | 6/1998 | Samson et al. | |
| 5,911,717 A | 6/1999 | Jacobsen et al. | |
| 5,935,437 A | 8/1999 | Whitmore | |
| 5,954,682 A | 9/1999 | Petrus | |
| 6,296,632 B1 | 10/2001 | Lüscher et al. | |
| 6,299,590 B1 | 10/2001 | Lüscher et al. | |

FOREIGN PATENT DOCUMENTS

| | | | |
|---|---|---|---|
| GB | 0049135 * | 8/2000 | 604/891.1 |
| JP | 61-161220 | 7/1986 | |
| JP | 2-280768 | 11/1990 | |
| JP | 2-280769 | 11/1990 | |
| JP | 2-280770 | 11/1990 | |
| JP | 2-280771 | 11/1990 | |
| JP | 4-20348 | 1/1992 | |
| JP | 4-197359 | 7/1992 | |
| JP | 5-208917 | 8/1993 | |
| WO | WO 91/13592 | 9/1991 | |
| WO | WO 93/00127 | 1/1993 | |
| WO | 5-504695 | 7/1993 | |
| WO | WO 94/16632 | 8/1994 | |
| WO | WO 95/08291 | 3/1995 | |
| WO | WO 96/04954 | 2/1996 | |
| WO | WO 97/19643 | 6/1997 | |

OTHER PUBLICATIONS

Bernatchez et al., "Biotolerance of Semisolid Hydrophobic Biodegradable Poly (ortho ester) for Controlled Drug Delivery" Journal of Biomedical Materials Research; vol. 27, No. 5, pp. 677–681, May, 1993.

Rüfenacht, D.A. et al., "A Simple Propulsion–Chamber System for the 16 Gauge Approach"; Neuroradiology (1986) 28:355–358.

Marks, R., et al., "Principles of Weaving"; The Textile Institute Manchester, 1976, pp. 130–135.

Taki et al., "The Eleventh General Meeting of Japan Biomaterial Society Collection of Scripts for Presentation"; Oct. 1989, at Kyoto University, Chief of the 11$^{th}$ Meeting: Takao Yamamuro.

Ayumi, Igaku No. [SIC] "Embolization Technique of Cerebral Arterial Aneurysm Advantages and Disadvantages of Embolization Technique and Surgical Operation"; vol. 153, No. 11, p. 635, Jun. 1990, Ishiyaku Publishers, Inc.

Goto, K., et al., "A New Technique for Embolization of Cerebral Arteriovenous Malformations and Dural Arteriovenous Fistulae"; Neuroradiology (1991) 33 [Suppl]: 193–194.

Harper, Marion, et al., "Isobutyl 2–cyanoacrylate as an Osseous Adhesive in the Repair of Osteochrondral Fractures"; Journal of Biomedical Materials Research, vol. 17, pp. 167–177 (1983).

A. Polk et al., "Controlled Release of Albumin from Chitsan–Alginate Microcapsules," Journal of Pharmaceutical Sciences, vol. 83, No. 2 (Feb. 1994), pp. 178–185.

K. Kamath et al., "Biodegradable Hydrogels in Drug Delivery," Advanced Drug Delivery Reviews, 11 (1993), pp. 59–84.

Serbinenko, F.A., M.D. "Balloon Catheterization and Occlusion of Major Cerebral Vessels;"; J. Neurosurg, vol. 41, Aug. 1974, pp. 125–145.

Ayumi, Igaku, No. [SIC], "Situation of New Subspecialty of Neurosurgery"; vol. 154, No. 7, p. 432, Aug. 1990, Ishiyaku Publishers, Inc.

Goto, K., "Recent Advances and Future Problems of Interventional Neuroradiology"; Neurosurgeons 9:229–239, Sep. 1990.

* cited by examiner

SYSTEM FOR IMPLANTING A CROSS-LINKED POLYSACCHARIDE FIBER AND METHODS OF FORMING AND INSERTING THE FIBER

This is a division of U.S. application Ser. No. 08/919,107, filed Aug. 28, 1997 now U.S. Pat. No. 6,139,520, which is a continuation-in-part application of U.S. application Ser. No. 08/776,943, filed Apr. 21, 1997 now U.S. Pat. No. 6,296,632, which is an application under 35 U.S.C. §371 of PCT/CH95/00184, filed Aug. 16, 1995, the entire disclosures of which are incorporated herein by reference.

BACKGROUND OF THE INVENTION

1. Field of the Invention

The present invention relates to implant systems and methods of forming and inserting a fiber. More particularly, the present invention relates to systems and methods for mixing a liquid including polysaccharide and a liquid including a cross linking agent to form a cross linked polysaccharide fiber.

2. Description of Related Art

Alginate is a polysaccharide material derived from brown seaweed. Although the predominate use of alginates is as a food additive to thicken and stabilize solutions, they are also used in various medical applications. Alginate can be easily cross linked into biocompatible hydrogels used as a cell immobilization matrix for various biotechnology applications. In addition, this substance can be used as a biodegradable gel/film coating in pharmaceutical applications. Alginate is also used to make wound dressings and pads capable of absorbing wound exudate and providing a moisture permeable wound covering.

By coming in contact with different ionic substances having certain affinities, alginate and other polysaccharides can exist in either a liquid or solid phase. In addition, alginates and other polysaccharides are capable of being reversibly cross linked so that they can either degrade or cross link on demand. The present invention relies on the ability of these materials to cross link on demand.

The inventors have discovered that alginate and other polysaccharides are particularly useful materials for forming a biocompatible implant. In addition, the inventors have discovered that implants formed of these materials are particularly useful in the treatment of intracranial aneurysms.

Intracranial aneurysms are extremely difficult to treat because they are often formed in remote cerebral blood vessels, which are very difficult to access. If left untreated, hemodynamic forces of normal pulsatile blood flow can rupture fragile tissue in the area of the aneurysm causing a stroke. In one type of treatment, coils are implanted in the body of a patient in an attempt to occlude blood flow to the aneurysm. However, this procedure is time consuming because it often requires bi-plane X-rays after placement of each coil. In addition, a procedurist normally needs to determine and select the proper size for the coils prior to implantation. Also, coils can compact over time because they fill approximately 40% of the aneurysm volume only.

In light of the foregoing, there is a need in the art for an improved implant and systems and methods for forming and implanting this implant.

SUMMARY OF THE INVENTION

Accordingly, the present invention is directed to systems and methods that substantially obviate one or more of the limitations of the related art. To achieve these and other advantages and in accordance with the purpose of the invention, as embodied and broadly described herein, the invention includes an implant system including a first reservoir containing a first liquid including polysaccharide, and a second reservoir containing a second liquid including an ionic cross linking agent. The system also includes a cannula including a first lumen in fluid communication with the first liquid in the first reservoir, a second lumen in fluid communication with the second liquid in the second reservoir, a distal end portion wherein the first and second lumens fluidly communicate with one another to mix the first and second liquids and thereby form a cross linked elongate fiber, and an opening in the distal end portion allowing passage of the cross linked fiber therethrough.

In another aspect, the present invention includes a method of forming an implant in a body. The method includes introducing a cannula into the body, the cannula including a first lumen, a second lumen, and an opening in a distal end portion of the cannula. The first liquid is passed through the first lumen, and the second liquid is passed through the second lumen. The method also includes mixing the first and second liquids in the cannula to form a flexible cross linked fiber, moving the fiber through the opening in the cannula, and contacting the fiber against body tissue to allow the fiber to bend and to form the implant in the body.

In another aspect, the invention includes a method of forming a fiber for an implant. The method comprises passing the first liquid through a tubular member placed in a reservoir containing the second liquid, and flowing the first liquid into the second liquid via an opening in a distal end portion of the tubular member. The polysaccharide and the ions of the cross linking agent then cross link to form an elongate fiber.

In an aspect of the invention, the polysaccharide of the first liquid includes alginate, and the cross linking agent of the second liquid includes calcium.

In an additional aspect, the system for inserting the fiber includes a spool having fiber wound thereon, a chamber containing the spool, the chamber having an interior, a first opening, and a second opening, and a syringe including a barrel in fluid communication with the first opening and a plunger movable in the barrel, movement of the plunger in the barrel pressurizing the interior of the chamber to deliver the fiber through the second opening.

In a further aspect, a cutter is provided on the cannula to sever a portion of the fiber passing through the lumen and opening of the cannula.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
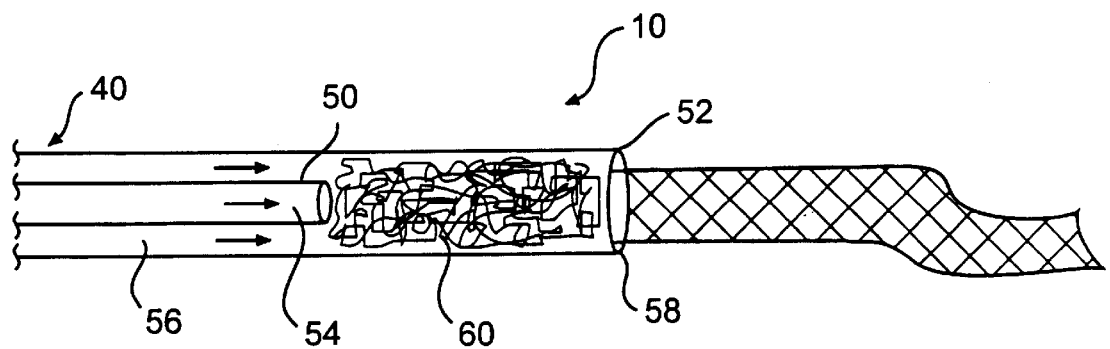
FIG. 1 is a view of a distal end portion of a cannula of a first embodiment of the invention.

Reference will now be made in detail to the present preferred embodiments of the invention, examples of which are illustrated in the accompanying drawings. Wherever possible, the same reference numbers are used in the drawings and the description to refer to the same or like parts, and the same reference numerals with alphabetical suffixes are used to refer to similar parts.

Figure 2:
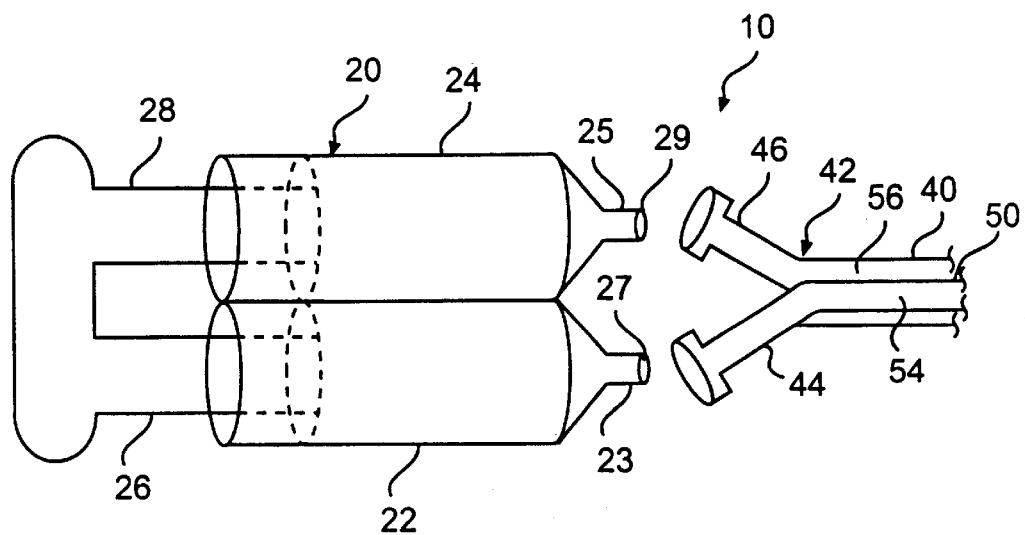
FIG. 2 is a view of a proximal end portion of the cannula of FIG. 1 and a dual barrel syringe for coupling to the cannula.

In accordance with the invention, there is provided an implant system including first and second reservoirs and a cannula having first and second lumens. FIGS. 1 and 2 respectively show distal and proximal end portions of a first embodiment of a system 10 in accordance with the present invention. As shown in FIG. 2, the system 10 includes a syringe 20 and a cannula 40 capable of being coupled together to introduce substances from the syringe 20 into the cannula 40.

The syringe 20 includes a first barrel 22 having a tip 23 formed with a discharge opening 27 and a second barrel 24 having a tip 25 formed with a discharge opening 29. The first and second barrels 22 and 24 respectively form a first reservoir containing a first liquid and a second reservoir containing a second liquid.

Preferably, the first liquid includes a polysaccharide, such as alginate (i.e., sodium alginate, potassium alginate, barium alginate, magnesium alginate, or strontium alginate, or mixtures thereof), chitosan, or a carboxylic acid containing polysaccharide. The second liquid preferably includes an ionic cross linking agent. When the polysaccharide of the first liquid is alginate, the ionic cross linking agent of the second liquid includes polyvalent cations, such as divalent cations. When the first liquid includes chitosan, the second liquid includes a compatible ionic cross linking agent, such as polyacrylic acid, heparin, or sodium carboxymethyl cellulose. For example, the first liquid is preferably a liquid including sodium alginate, and the second liquid is preferably a liquid solution including calcium, such as a liquid solution including calcium chloride, calcium gluconate, or calcium sulfate, or mixtures thereof.

As described below, the polysaccharide and the cross linking agent form a cross linked polysaccharide fiber when they are mixed in the cannula 40. The first and second barrels 22 and 24 are preferably separate from one another to prevent this cross linking from taking place in the syringe 20.

The syringe 20 also includes a first plunger 26 movable in the first barrel 22 and a second plunger 28 movable in the second barrel 24. Preferably, the first and second plungers 26 and 28 are coupled together so that they move together in the respective barrels 22 and 24 to eject the first and second liquids simultaneously from the discharge openings 27 and 29. As compared to separate plunger arrangements, the coupled first and second plungers 26 and 28 make it easier for a user to eject the first and second liquids at constant rates to form a more consistent cross linked fiber.

As shown in FIG. 2, the proximal end portion of the cannula 40 includes an adapter 42 having first and second branches 44 and 46 capable of being coupled directly to the respective tips 23 and 25. Although the first and second branches 44 and 46 are preferably coupled directly to the tips 23 and 25, other coupling arrangements are possible. For example, separate lengths of flexible tubing could be provided to couple the tips 23 and 25 and the branches 44 and 46 fluidly together. In addition, the first and second branches 44 and 46 could be located at different locations on the cannula 40 without both being on the same adapter 42.

Preferably, the cannula 40 is a catheter having sufficient flexibility to allow for insertion into predetermined areas in a body. For example, the cannula 40 could be a flexible catheter, such as a micro catheter sufficiently flexible to be inserted into the cranial area to treat an aneurysm. In addition, the cannula 40 could be an endoscopic device, needle, or any other type of medical device having a generally tubular shape. Although the cannula 40 is preferably formed of a polymer, other materials, such as metal, can be used. To allow for imaging in the body, the cannula 40 preferably includes a portion or portions including radiopaque material.

As shown in FIG. 1, the cannula 40 includes a first tubular portion 50, a second tubular portion 52, and an opening 58 formed in the distal end of the cannula 40. The first tubular portion 50 is positioned coaxially within the second tubular portion 52 to form a first lumen 54 in the first tubular portion 50, and a second lumen 56 between an outer surface of the first tubular portion 50 and an inner surface of the second tubular portion 52. When the syringe 20 shown in FIG. 2 is coupled to the adapter 42 on the cannula 40, the first lumen 54 is placed in fluid communication with the first liquid in the first barrel 22, and the second lumen 56 is placed in fluid communication with the second liquid in the second barrel 24.

The first lumen 54 extends from the first branch 44 shown in FIG. 2 to its distal end shown in FIG. 1, and the second lumen 56 extends from the second branch 46 shown in FIG. 2 to its distal end shown in FIG. 1. Although the first and second lumens 54 and 56 are coaxially arranged and formed by the first and second tubular portions 50 and 52, other configurations are possible. For example, the first and second lumens could be parallel lumens having independent axes and feeding into a single lumen segment (mixing chamber) at the distal tip portion of the catheter.

The distal end of the second tubular portion 52 extends further in the distal direction than the distal end of the first tubular portion 50. This staggered end relationship of the tubular portions 50 and 52 forms a mixing chamber 60 in the distal end portion of the cannula 40 between the first tubular portion 50 and the opening 58. The first and second lumens 54 and 56 communicate with one another in the mixing chamber 60. As the first and second liquids flow from the first and second lumens 54 and 56 to the mixing chamber 60, these liquids mix and form the cross linked polysaccharide fiber in the mixing chamber 60. The resulting fiber is flexible and has a diameter substantially the same as that of the inner surface of the second tubular portion 52. After the fiber is formed, it is extruded from the cannula 40 via the opening 58.

Preferably, the first liquid contained in the first barrel 22 of the syringe 20 is a solution including a polysaccharide, such as sodium alginate, and the second liquid contained in the second barrel 24 of the syringe 20 is a solution including an ionic cross linking agent, such as calcium (i.e. calcium chloride) or some other cross linking agent having divalent ions. For example, when sodium alginate and calcium chloride combine in the mixing chamber 60, the divalent cations (calcium ions) replace the sodium ions to form a cross linked, hydrogel, alginate fiber. Because the resulting cross linked alginate fiber is a hydrogel, it is possible to capture certain contrast substances into the gel to make the fiber visible in MRI, CT, and fluoroscopy.

For example, radiopaque substances, such as tantalum, tungsten, barium sulfate, and/or titanium dioxide can be added to the first liquid and/or the second liquid to make the formed fiber radiopaque. In addition, barium, which is a divalent cation, can be used to cross link with the polysaccharide and make it radiopaque. Certain solutions of iodine and/or gadolinium can also be solubilized in the liquid including polysaccharide prior to cross linking and may remain trapped within the gel after cross linking, making it visible in certain imaging modalities. In particular, gadopentetate dimeglumine and/or iothalamate meglumine, which are water soluble salts used as contrast agents, can be combined with the polysaccharide to produce a gel visible in both MRI and x-ray modalities (fluoroscopy, CT, DSA).

Certain drugs can also be added to the first and second liquids prior to forming the fiber. These drugs can also be captured in the cross linked fiber as it forms in the mixing chamber 60. After implantation of the fiber in the body, the drugs are preferably released over time to provide particular treatments. For example, alcohol could be added to the first and/or second liquid to provide a fiber capable of treating an arteriovenous malformation (AVM)—an abnormal network of vessel connections between an artery and vein. In addition, thrombogenic substances could be added to one of the liquids to form a fiber capable of inducing thrombosis in an aneurysm cavity.

A precipitating material can also be added to the first liquid and/or the second liquid prior to forming the fiber. The precipitating material precipitates and forms a matrix as the fiber is formed. This matrix preferably holds portions of the fiber together to stabilize the implant structure formed by the fiber and to prevent fiber migration in the body. For example, polyvinyl alcohol, sucrose acetate, or cellulose acetate could be added to the first liquid and/or the second liquid to form the matrix. The matrix may be desired when using the fiber to pack a cavity, such as an aneurysm sac.

Alternatively, an adhesive material, such as cyanoacrylate adhesive, could be added to the first liquid and/or second liquid so that portions of the fiber adhere to one another after implant formation. This adherence stabilizes the implant and prevents fiber migration, especially when packing a cavity.

When the first liquid includes alginate, the first liquid and/or the second liquid also may include a different polysaccharide, such as chitosan. Chitosan forms an electrostatic interaction with alginate. When a cross linked alginate fiber is formed, chitosan and alginate form a polymer entanglement to provide structural integrity.

Figure 3:
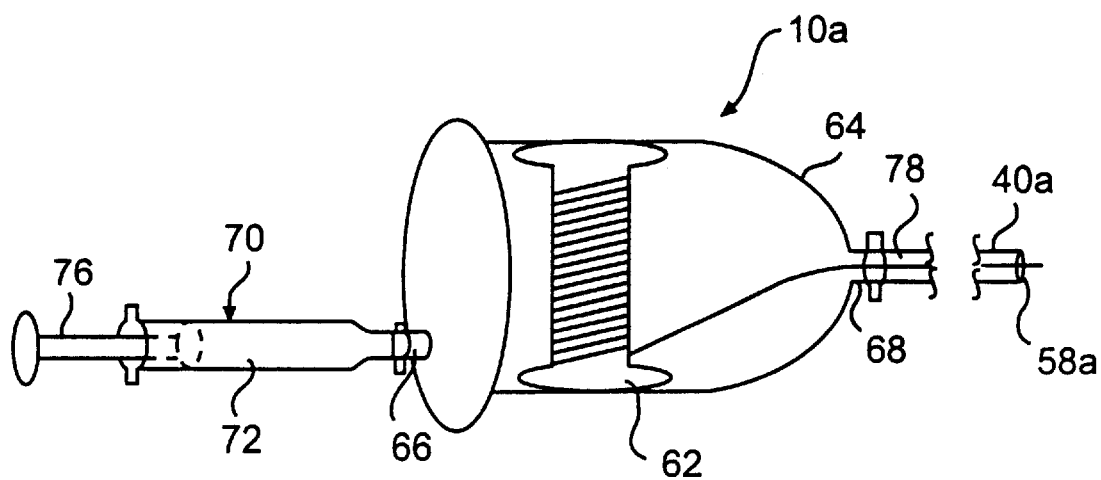
FIG. 3 is a view of a chamber, syringe, and cannula of a second embodiment of the invention.

FIG. 3 shows a system 10a for implanting a fiber in the body in accordance with a second embodiment of the invention. The system 10a includes a spool 62 having fiber wound thereon and a chamber 64 containing the spool 62. Preferably, the fiber on the spool 62 is a cross linked polysaccharide fiber, such as a cross linked alginate fiber, similar or identical to the fiber formed by the system 10 described above. The spool 62 is mounted in an interior of the chamber 64 so that the spool 62 is capable of rotating about its axis to unwind the fiber from the spool 62.

The chamber 64 includes a first adapter 66 and a second adapter 68 having respective openings in fluid communication with the interior of the chamber 64. As shown in FIG. 3, the system 10a also includes a syringe 70 having a barrel 72 coupled to the first adapter 66, and a cannula 40a having a proximal end hub coupled to the second adapter 68. The syringe barrel 72 and interior of the chamber 64 contain a carrier fluid, such as saline solution, for conveying the fiber. A movable plunger 76 in the barrel 72 of the syringe 70 ejects the carrier fluid from the barrel 72 to the chamber 64.

When the plunger 76 of the syringe 70 forces carrier fluid into the chamber 64, the carrier fluid in the chamber 64 becomes pressurized and flows through the second adapter 68 and cannula 40a. As the carrier fluid flows from the chamber 64, it conveys the fiber along with it. The fiber moves because the pressure of the carrier fluid in the chamber 64 is greater than the pressure in a distal end portion of cannula 40a and because friction exists between the carrier fluid and the fiber. Initially, the carrier fluid conveys the free end of the fiber through the second adapter 68 and cannula 40a. Then, the carrier fluid continues the conveyance of the fiber while the spool 62 rotates to unwind the fiber.

The cannula 40a includes at least one lumen 78 and an opening 58a in a distal end portion for allowing passage of the fiber therethrough. Because the cannula 40a only requires a single lumen, it can be small enough and flexible enough to reach distal cerebral vasculature: Although the cannula 40a preferably includes a single lumen rather than a plurality of lumens, it is otherwise constructed like the cannula 40 described in connection with the first embodiment. In other words, the cannula 40a can be a flexible catheter, micro catheter, endoscopic device, needle, or any other medical device having a generally tubular shaped portion.

Placing the spool 62 in the chamber 64 rather than in the barrel 72 allows for the use of both a smaller syringe and a larger compartment for holding the fiber, as compared to an arrangement wherein the spool is placed in the syringe barrel itself.

Figure 4:
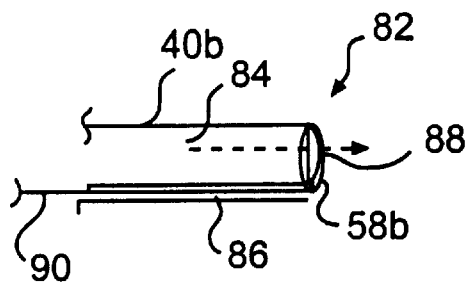
FIG. 4 is a view of a cutter for the cannulas shown in FIGS. 1 and 2 and FIG. 3.

FIG. 4 shows an embodiment of the invention including a cutter 82 for severing the fiber. The cutter 82 is on a distal end portion of a cannula 40b including a primary lumen 84, an auxiliary lumen 86, and a distal opening 58b. With the exception of the auxiliary lumen 86, the cannula 40b is preferably constructed like the cannula 40 shown in FIGS. 1 and 2, the cannula 40a shown in FIG. 3, or one of the cannulas disclosed in above-mentioned U.S. patent application Ser. No. 08/776,943, the disclosure of which has been incorporated by reference.

The cutter 82 is preferably a strand of wire having a loop shaped portion 88 and a substantially straight actuator portion 90 extending from the loop shaped portion 88. The loop shaped portion 88 is positioned in the distal end portion of the cannula 40b along an inner surface of the lumen 84 so that the loop shaped portion 88 surrounds the fiber when the fiber passes through the lumen 84 and the opening 58b. The actuator portion 90 extends through the auxiliary lumen 86 to a proximal end portion of the cannula 40b. Alternatively, the actuator portion 90 extends through the primary lumen 84 or on the outside of the cannula 40b when the cannula does not have an auxiliary lumen.

Figure 5A:
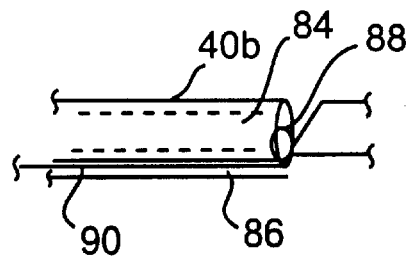
FIG. 5a and 5b are views showing how the cutter of FIG. 4 severs a fiber.
Figure 5B:
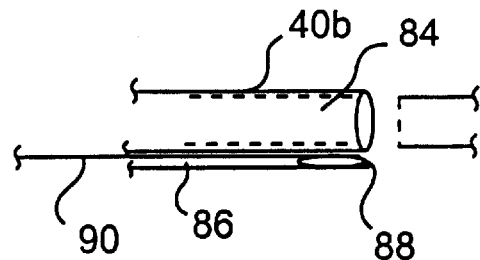

FIGS. 5a and 5b show how the cutter 82 severs the fiber after a desired length of fiber has passed through the opening 58b. As shown in FIG. 5a, when the actuator 90 is moved in the proximal direction with respect to the cannula 40b, the loop shaped portion 88 passes across the lumen 84 and through the fiber to begin severing the fiber. Continued pulling of the actuator 88, completely severs the fiber, as shown in FIG. 5b, and places the loop shaped portion in the auxiliary lumen 86.

Figure 6:
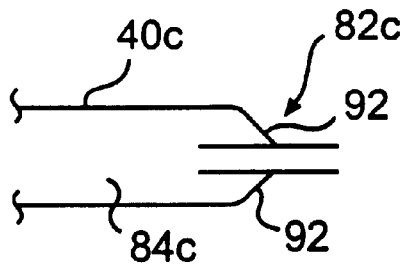
FIG. 6 is a view of an alternate embodiment of a cutter for the cannulas shown in FIGS. 1 and 2 and FIG. 3.
Figure 7:
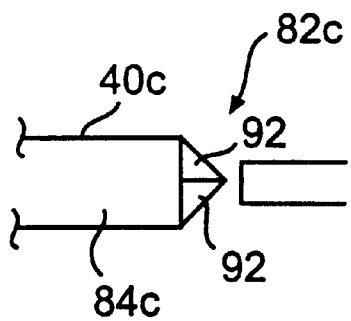
FIG. 7 is a view of the cutter of FIG. 6 after the cutter severs a fiber.
Figure 8:
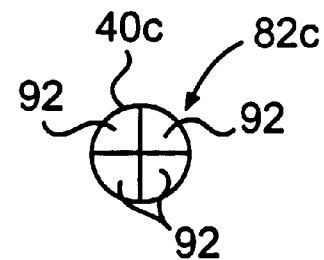
FIG. 8 is a distal end view of the cutter of FIG. 7.

FIGS. 6, 7, and 8 show an alternate embodiment of a cutter 82c for severing the fiber. The cutter 82c is mounted on a cannula 40c constructed like the cannula 40 shown in FIGS. 1 and 2, the cannula 40a shown in FIG. 3, or one of the cannulas disclosed in above-mentioned U.S. patent application Ser. No. 08/776,943. The cannula 40c includes a lumen 84c allowing for passage of the fiber therethrough.

As shown in the distal end view of FIG. 8, the cutter 82c includes a plurality of resilient flaps or leaflets 92 biased toward one another to form a compliant slit valve. The leaflets 92 move away from one another in response to movement of the fiber against an inner surface of the leaflets 92 and increased fluid pressure in the lumen 84c generated by the syringe 20 shown in FIG. 2 or the syringe 70 shown in FIG. 3. As shown in FIG. 6, sufficient pressure of the fiber and fluid in the lumen 84c forces the leaflets 92 away from one another to create an opening having a size sufficient to allow for passage of the fiber from the distal end portion of the cannula 40c. When this pressure is reduced, the leaflets 92 resiliently close on the fiber to sever or pinch off the fiber, as shown in FIG. 7.

In an alternate embodiment, the adapter 42, shown in FIG. 2, is configured to allow an operator to move the first tubular portion 50, shown in FIGS. 1 and 2, axially in the second tubular portion 52. With such an arrangement, the first tubular portion 50 may be moved axially toward the distal opening 58 to push the formed fiber from the mixing chamber 60 and thereby separate the fiber from the cannula 40.

Methods of forming an implant in a body are discussed below with reference to FIGS. 1–4, 5a, 5b, and 6–8. Although the invention is described in connection with the structure shown in these figures, it should be understood that the invention in its broadest sense is not so limited.

Initially, the distal end portion of the cannula 40 shown in FIGS. 1 and 2 is inserted in the body of a patient and the distal end is guided to a site where the implant is to be formed. To facilitate the insertion, a guide wire is inserted in the first lumen 54 and the cannula 40 is moved over the guide wire. In addition, the movement of the cannula 40 can be monitored fluoroscopically.

When the cannula is properly positioned, the syringe 20 is coupled to the adapter 42. Then, the plungers 26 and 28 are moved simultaneously in the barrels 22 and 24 to eject the first and second liquids respectively through the lumens 54 and 56 and into the mixing chamber 60. In the mixing chamber 60, the polysaccharide, such as alginate, and the ionic cross linking agent mix, and the ions of the cross linking agent cross link with the polysaccharide to form the cross linked polysaccharide fiber in the mixing chamber 60. For example, when the first liquid includes sodium alginate and the second liquid includes calcium chloride, a cross linked alginate fiber forms in the mixing chamber 60. The resulting fiber is flexible and has an outer surface matching the inner surface of the second tubular portion 52. As the fiber is formed, the fiber is ejected from the cannula 40 via the opening 58.

Since the fiber is formed inside the cannula 40, the fiber is one continuous piece as it is injected into a vessel or a cavity. If the injection of both the first and second liquids continue, the fiber continues to form as one piece and is extruded out the end of the cannula 40. This allows the fiber to stay together and reduces the chance of embolization. As the fiber passes from the cannula 40, the fiber contacts tissue and curls up on itself inside the cavity it is filling to form a ball or nest shaped implant structure. Preferably, the consistency of the cross linked alginate fiber is soft enough to allow dense packing inside the cavity.

As mentioned above, an agent, such as tantalum, tungsten, barium sulfate, and/or titanium dioxide, can be added to at least one of the first and second liquids to make the resulting fiber radiopaque. As the fiber is formed, a procedurist can monitor the formation and implantation of the fiber via imaging equipment.

The fiber can be delivered via the cannula 40, shown in FIGS. 1 and 2, or the cannula 40a, shown in FIG. 3, into a blood vessel to occlude the vessel partially or completely. For example, the fiber could be delivered into a blood vessel leading to an aneurysm to limit blood flow to the aneurysm by occluding the vessel. The fiber could also be used to treat an AVM by delivering the fiber into a vessel leading to the AVM to limit blood flow to the AVM.

In a preferred method, the distal end of the cannula 40, shown in FIGS. 1 and 2, or the cannula 40a, shown in FIG. 3, is placed adjacent to an aneurysm and the cross linked fiber is ejected to fill the sac or cavity of the aneurysm at least partially. When the fiber contacts tissue in the cavity it curls back on itself making a ball or nest of fiber that provides packing in the cavity. This ball or nest of fiber is able to fill an irregularly shaped sac completely. When the fiber includes alginate, the alginate material provides a biocompatible surface at the aneurysm neck for endothelial cell growth. In addition, the fiber mass limits blood flow to the aneurysm and protects the fragile aneurysm wall from rupturing since it is no longer exposed to the hemodynamic forces of the normal pulsatile blood flow.

Preferably, the first liquid and/or the second liquid include a precipitating material or an adhesive when the fiber is delivered to fill an aneurysm sac or cavity. The precipitating material forms a matrix for holding the fiber implant together, and the adhesive adheres portions of the fiber to one another. This maintains the implant in the sac and prevents fiber migration in the body.

Because the fiber is flexible, the nest or ball of fiber is more dense than a rigid metal coil and fills a higher percentage of volume of the blood vessel or the aneurysm cavity. As mentioned above, a thrombogenic substance can be added to one of the first and second liquids. When a fiber having this substance is implanted in an aneurysm cavity, it releases the thrombogenic substance to induce thrombosis in the cavity.

As compared to some gels used to fill aneurysms, it is easier to control the volume of fiber. In addition, the fiber fills the cavity more completely to minimize leakage and may take up more volume than beads of gel. Also, the fiber preferably does not embolize rapidly.

In another method, the distal end of the cannula 40, shown in FIGS. 1 and 2, or the cannula 40a, shown in FIG. 3, is inserted into the body and used to deliver the fiber into soft tissue to provide bulking of the soft tissue. For example, the fiber could be delivered next to the urethral sphincter to provide bulking for the treatment of bladder incontinence.

The dual barrel syringe 20 shown in FIG. 2 allows for constant infusion of both the first liquid and the second liquid to the mixing chamber 60 shown in FIG. 1. Because the fiber is formed in the mixing chamber 60 of the cannula 20 itself, there is no need to manufacture the fiber separately, install it in a delivery device, and use a carrier fluid.

When using the system 10 shown in FIGS. 1 and 2, the length of fiber filling the body cavity does not need to be pre-determined. The fiber continues to form as long as the first and second liquids are injected. The cutter 82 shown in FIGS. 4, 5*a*, and 5*b* or the cutter 82*c* shown in FIGS. 6–8 can be used to sever the implanted portion of the fiber from the portion of fiber residing in the mixing chamber 60. When the first tubular portion 50, shown in FIGS. 1 and 2, is axially movable in the second tubular portion 52, the first tubular portion 50 may be moved axially toward the distal opening 58 to push the formed fiber from the mixing chamber 60 and thereby separate the fiber from the cannula 40.

A method of forming a fiber is discussed below with reference to FIG. 9. Although this aspect of the invention is described in connection with the structure shown in this figure, it should be understood that the invention in its broadest sense is not so limited.

Figure 9:
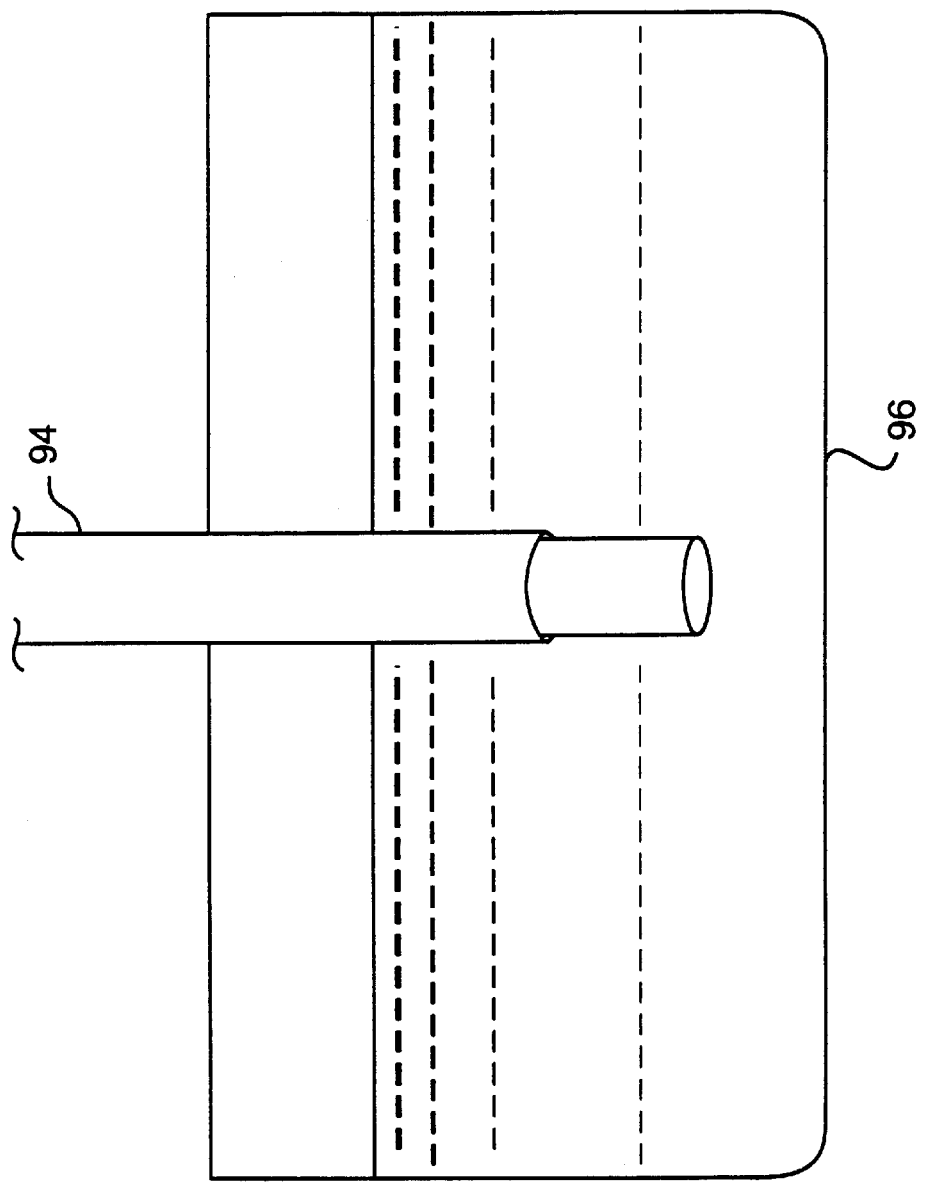
FIG. 9 is a view of a tubular member and reservoir used to form a fiber contained in the chamber shown in FIG. 3.

FIG. 9 shows a tubular member 94 and a reservoir 96 used in the manufacture of a cross linked polysaccharide fiber for the system 10*a* shown in FIG. 3 or for one of the fiber delivery devices disclosed in above-mentioned U.S. patent application Ser. No. 08/776,943. The tubular member 94 is coupled to a source of liquid including polysaccharide, such as a liquid including alginate (sodium alginate), and the reservoir 96 contains a liquid including an ionic cross linking agent, such as a liquid including calcium chloride or a liquid solution including other divalent cations.

The liquid including polysaccharide flows through the tubular member 94 and into the liquid including cross linking agent in the reservoir 96 via an opening in a distal end portion of the tubular member 94. As the liquid including polysaccharide flows from the tubular member 94 and contacts the cross linking agent, the cross linked polysaccharide fiber forms. The formed fiber has an outer surface shape similar to the inner surface shape of the opening and lumen in the tubular member 94. When the fiber increases in length, it can be wound on a spool, such as the spool 62 shown in FIG. 3, and then loaded in a delivery device, such as the system 10*a* shown in FIG. 3, or one of the fiber delivery devices disclosed in above-mentioned U.S. patent application Ser. No. 08/776,943.

Varying the size of the tubular member 94 and flow of the liquid in the tubular member 94 can control the composition, size, and consistency of the cross-linked fiber. Radiopaque substances can be added to the liquid flowing in the tubular member 94 and/or to the liquid in the reservoir 96 to render the cross linked fiber radiopaque. In addition, one or more drugs can be added to one or both liquids to enable drug delivery via the formed fiber. Chitosan can also be added to one or both of the liquid to provide structural integrity to the fiber.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A method of manufacture comprising:

passing a first liquid including polysaccharide through a tubular member placed in a reservoir containing a second liquid including an ionic cross linking agent;

flowing the first liquid into the second liquid via an opening in a distal end portion of the tubular member;

cross linking the polysaccharide and the ions of the cross linking agent to form an elongate fiber; and loading a fiber dispenser with the elongate fiber, the fiber dispenser being configured to be part of a system for implanting the elongate fiber into a body, wherein the fiber dispenser comprises a spool, and wherein the loading comprises winding the elongate fiber on the spool.

2. The method of claim 1, wherein the first liquid includes alginate.

3. The method of claim 1, wherein at least one of the first liquid and the second liquid includes chitosan.

4. The method of claim 1, wherein the first liquid includes sodium alginate.

5. The method of claim 1, wherein the second liquid includes calcium chloride.

6. The method of claim 1, further comprising adding a radiopaque substance to at least one of the first and second liquids.

7. The method of claim 6, wherein the radiopaque substance includes at least one of tantalum, tungsten, barium sulfate, and titanium dioxide.

8. The method of claim 1, further comprising adding a drug to at least one of the first and second liquids.

9. The method of claim 1, wherein the method further comprises associating the loaded fiber dispenser with other parts of the system for implanting the elongate fiber into a body.

\* \* \* \* \*